(12) United States Patent
Lee (10) Patent No.: US 8,075,564 B2
(45) Date of Patent: Dec. 13, 2011

(54) PIEZOTOME FOR MAXILLARY SINUS OPERATION

(76) Inventor: Dal Ho Lee, Seoul (KR)

( * ) Notice: Subject to any disclaimer, the term of this patent is extended or adjusted under 35 U.S.C. 154(b) by 77 days.

(21) Appl. No.: 12/313,591

(22) Filed: Nov. 21, 2008

(65) Prior Publication Data

US 2009/0326440 A1  Dec. 31, 2009

(30) Foreign Application Priority Data

Jun. 26, 2008  (KR) .................. 10-2008-0060643

(51) Int. Cl.
*A61B 17/00* (2006.01)
*A61C 3/02* (2006.01)

(52) U.S. Cl. .......................... 606/80; 433/144

(58) Field of Classification Search .............. 433/86, 433/118–122, 144, 150, 164, 197–198, 226; 623/17.17–17.18; 606/79–85; 30/355–357, 30/346.55; 125/19, 16.01, 22
See application file for complete search history.

(56) References Cited

U.S. PATENT DOCUMENTS

| | | | | |
|---|---|---|---|---|
| 4,251,213 A * | 2/1981 | Paquette | ........................ | 433/144 |
| 4,832,683 A * | 5/1989 | Idemoto et al. | ................. | 604/22 |
| 6,171,312 B1 | 1/2001 | Beaty | | |
| 6,204,592 B1 | 3/2001 | Hur | | |
| 6,312,256 B1 * | 11/2001 | Dieras et al. | .................. | 433/119 |
| 6,722,882 B2 * | 4/2004 | Buchanan | ...................... | 433/119 |
| 6,740,090 B1 * | 5/2004 | Cragg et al. | ...................... | 606/79 |
| D509,588 S * | 9/2005 | Vercellotti et al. | ........... | D24/144 |
| D509,899 S * | 9/2005 | Vercellotti et al. | ........... | D24/144 |
| 7,125,253 B2 | 10/2006 | Kitamura et al. | | |
| D539,908 S * | 4/2007 | Vercellotti et al. | ........... | D24/144 |
| D539,909 S * | 4/2007 | Vercellotti et al. | ........... | D24/144 |
| D576,729 S * | 9/2008 | Tanaka et al. | ................. | D24/144 |
| 7,481,652 B2 * | 1/2009 | Senia et al. | .................... | 433/102 |
| 2002/0182565 A1 * | 12/2002 | Senia et al. | .................... | 433/102 |
| 2007/0015102 A1 * | 1/2007 | Vercellotti et al. | ............. | 433/2 |
| 2008/0161934 A1 * | 7/2008 | Yamada | ..................... | 623/17.17 |
| 2009/0004624 A1 * | 1/2009 | Lee | ................ | 433/144 |
| 2009/0326535 A1 * | 12/2009 | Blus | ............................... | 606/80 |

FOREIGN PATENT DOCUMENTS

| | | | |
|---|---|---|---|
| KR | 200365219 Y1 | | 10/2004 |
| KR | 100757002 B1 | | 9/2007 |
| KR | 200365219 Y1 | * | 2/2009 |

* cited by examiner

*Primary Examiner* — Thomas C Barrett
*Assistant Examiner* — Zade Coley
(74) *Attorney, Agent, or Firm* — Galgano & Associates, PLLC; Thomas M. Galgano; Jessica G. Bower (57) ABSTRACT

A piezotome operation unit for lifting a maxillary sinus at a position of placement of an implant upon lifting the maxillary sinus, which forms and enlarges the vertical hole with ease in a remaining bone of the maxillary sinus though vertical approaching, and upon forming a lateral window below a malar bone through lateral approaching, prevents a maxillary membrane from becoming damaged, thereby ensuring continuous, safe lifting so that the operating time is shortened and the efficiency of the operation is maximized.

8 Claims, 7 Drawing Sheets

ly lifting, at a position of placement of an implant upon

PIEZOTOME FOR MAXILLARY SINUS OPERATION

TECHNICAL FIELD

The present invention relates to a piezo ultrasonic surgery unit, which is hereinafter referred as a 'piezotome operation unit', for lifting a maxillary sinus, and more particularly, to a piezo operation unit which at a position of placement of an implant upon lifting of a maxillary sinus, can form and enlarge a vertical hole with ease in a remaining bone of the maxillary sinus though vertical approaching, and upon forming a lateral window below a malar bone through lateral approaching, can prevent a maxillary membrane from being damaged, thereby ensuring continuous, safe lifting.

BACKGROUND ART

While implant generally means a replacement of a specific section of a human body, it means grafting of an artificial tooth in dentistry.

The implant is a hi-tech operation method by which upon the occurrence of loss of the root of a tooth, an artificial dental root made of titanium, which is not rejected by the human body, is implanted in alveolus from which the tooth was removed, and an artificial tooth then is fixed thereto to recover an original function of the tooth. In comparison with a common prosthesis or denture, which causes the neighboring teeth and bone to be damaged as time passes, the implant has advantages in that it does not have a bad influence on the neighboring tooth, and that it is usable for a long time since it prevents tooth decay while being of similar function and shape to that of the natural tooth.

However, it was reported that the success rate of the implant at the maxillary posterior teeth was comparatively lower than that for other parts. This is because the maxillary posterior teeth are weak and the maxillary sinus exists near the maxillary posterior teeth, so that a long implant cannot be placed into the maxillary posterior teeth.

That is, since the maxillary sinus existing in the maxillary is the space surrounded by a mucous membrane, when a tooth is lost, the maxillary sinus physiologically falls down and widens greatly and the downward extension of the maxillary sinus and the osteolysis owing to the loss of teeth occur, resulting in a lack in the amount of bone into which the implant can be placed, making it difficult to carry out the implantation for the maxillary posterior teeth.

Meanwhile, as a representative operating method of the related art in the case of the occurrence of a lack in the amount of bone up to the maxillary sinus, the two operating methods are as follows: a lateral approaching method in which a lateral window (hole) is formed below a malar bone, a maxillary membrane is directly lifted there through, and a graft material is filled between the inferior margin of the maxillary sinus and the maxillary membrane; and a vertical approaching method using an osteotome.

First, the lateral approaching method is an operating method for the placement of a long implant at a maxillary posterior tooth, which is greatly deficient in the amount of bone in a vertical direction (remaining bone is 5 mm or less), wherein the method is carried out so that a sidewall of a maxillary is removed in consideration of the height of the remaining maxillary extending up to the maxillary sinus 100, and the amount of bone is secured through bone grafting.

In specific, the lateral approaching method includes a process of harvesting bone fragments of a patient in order to graft a bone to a portion where the amount of a bone is deficient from a bone section other than the section to be operated on (if it is difficult to harvest bone fragments from the patient, artificial bone is used), a setting process of creating an incision line to a vestibular region of a section corresponding to a molar tooth, a forming process of forming a mucoperiosteal flap, a windowing process of windowing a facial wall of maxillary sinus through fracture line formed using a round bur, a piezo sawtooth, or a diamond tip, after windowing, a lifting process of lifting the facial wall of the maxillary sinus and a membrane of the maxillary sinus, a treating process of treating a space in the maxillary sinus whose bone plate is lifted, a grafting process of grafting a bone, a suturing process, and a placement process of placing an implant 6 to 12 months after the operation.

However, such a lateral approaching method is very difficult to do and is a careful, time-intensive process because especially during the windowing is the maxillary sinus often punctured in the process of using the round bur, the piezo sawtooth, or the diamond tip, resulting in the symptoms of swelling and pain.

Further, the vertical approaching method is an operating method implemented when the amount of the remaining bone is slightly deficient (e.g. 5 to 10 mm), wherein a bone is lifted using a chisel such as osteotome, or the remaining bone is removed using a special drill or reamer, an autogenous bone or an artificial bone is grafted into that space and an implant is placed there.

That is, the vertical approaching method is carried out so that a hole is formed using a drill at a portion where an implant is placed, osteotomes (each having diameters ranging in size from small to large) are inserted in a series into the hole and are hammered so as to gradually enlarge the hole, approach the maxillary membrane so as to fracture only a bone without damaging the membrane, an autogenous bone or an artificial bone is grafted in that space, and the implant is placed there.

In specific, the vertical method includes a process of forming the hole using a twist drill extending to a stable distance which does not however reach the maxillary membrane, i.e. up to a compact bone below the maxillary membrane, a process of sequentially inserting and hammering the osteotomes having diameters varying from a small size to a large size into the hole so as to form a hole corresponding to a diameter of the implant, and upon formation of the hole suitable to implant placement, a process of finally and carefully hammering the osteotome so as to fracture the compact bone, a process of filling the hole of the compact bone with a bone graft material, a process of softly hammering the osteotome into the hole filled with the bone graft material so as to lift the maxillary membrane, and then a process of removing the remaining bone using the special drill or reamer, a process of lifting the maxillary membrane using the graft material until a height of an available bone is secured such that the implant can be placed through that height, and a process of placing the implant.

However, despite that such a vertical approaching method has the advantage of few occurrences of edema occurring in patients after operation because of the narrow target section of the operation, a long time is spent operating since during operation a dentist cannot directly observe the maxillary membrane so that he must operate very carefully while checking the target section via X-ray, a patient feels very unpleasant owing to the striking which is done during the operation, and particularly when the drill comes into point contact with the maxillary membrane as the tip thereof rotates is a vertical load concentrated upon the contacted maxillary membrane thereby easily fracturing the same.

That is, while the special drill or reamer does not fracture the remaining bone of the maxillary membrane since it is not hammered (so that it causes only a little pain to the patient), it has a very small operating force so as to be insufficient to puncture the maxillary membrane, so that it takes too long of a time to remove the same. Further, if the maxillary membrane is of an irregular shape or is severely inclined, the drill or reamer can puncture the maxillary membrane while removing the remaining bone, making it difficult to maintain in place the bone graft material for forming the bone material. This allows the implant to be exposed to the outside in the maxillary membrane without being placed in the bone, thereby increasing the possibility of infection and degrading the capability of supporting the implant because of a lack in the amount of support bone.

Therefore, recently there has been proposed a piezoelectric device which has been known to be advantageous to the protection of the weak maxillary membrane upon the formation of a window or then the lifting of the maxillary membrane because unlike the existing method, it hardly punctures or tears the maxillary membrane even when coming into contact with the same. A conventional piezotome unit used in the piezoelectric device is an ultrasonic device which is bent like a "ㄱ" so that it can easily approach the maxillary sinus. However, since it has no structure for preventing the maxillary membrane from becoming damaged through a construction which does not excessively penetrate into the target section of the operation after removal of the remaining bone, it is impossible to implement lifting in a stable state, so that if a dentist applies an excessive force to the target section, the maxillary membrane is as a result frequently punctured. Therefore, there is a need to provide a piezotome unit capable of solving the above problems.

DISCLOSURE

Technical Problem

The present invention has been made to solve the foregoing problems with the prior art, and therefore an object of the present invention is to provide a piezotome operation unit for lifting a maxillary sinus, which at a position of placement of an implant upon lifting the maxillary sinus, can form and enlarge a vertical hole with ease in a remaining bone of the maxillary sinus though vertical approaching, and upon forming a lateral window below a malar bone through lateral approaching, can prevent a maxillary membrane from becoming damaged, thereby ensuring continuous, safe lifting so that the operation time is shortened and maximizing the efficiency of the operation.

TECHNICAL SOLUTION

In order to accomplish the above object of the present invention, according to an aspect of the present invention, there is provided a piezotome operation unit for lifting a maxillary sinus via vertical approaching, the unit including a piezo body, an end of which is fixedly inserted into a hand piece of a piezo main unit, a piezo pole extending in a linear or bent type from another end of the piezo body, and a piezo tip provided on an end of the piezo pole and having a plurality of cutting blades arranged at regular intervals, wherein a water supply hole is provided at the center of the inside of the piezotome operation unit in a manner so as to pass through the piezo body, the piezo pole, and the piezo tip, and a stopper protrudes from an outer face of the piezo pole so as to restrict the distance of insertion in accordance with the thickness of the remaining bone.

The cutting blades may be shaped like a hemisphere in which respective ends thereof converge towards a leading end side.

In another embodiment of the invention, there is provided a piezotome operation unit for lifting a maxillary sinus via vertical approaching, the unit including a window body, an end of which is fixedly inserted into a hand piece of a piezo main unit, a window pole extending in a linear or bent fashion from another end of the window body such that the window pole easily approaches the maxillary sinus, and a window tip provided on an end of the window pole and having a plurality of cutting projections for the insertion of a graft material, wherein a water supply hole is provided at the center of the inside of the piezotome operation unit in a manner so as to pass through the window body, the window pole, and the window tip, and a stopper protrudes from an outer face of the window pole so as to, upon forming a lateral window below a malar bone, prevent the transmission of an excessive load to the maxillary sinus.

The window tip may be shaped like an inverted triangle which is gradually enlarged from a lower portion towards an upper portion.

The cutting projections may be provided on an end of the window tip so as to be arranged linearly at equal intervals such that the respective projection is shaped like a triangle in which opposite upper sides thereof are formed with inclined cutting faces meeting at an apex.

The water supply hole may be shaped like a Y, an end of which branches out in two directions.

ADVANTAGEOUS EFFECTS

According to the present invention, the piezotome operation unit for lifting a maxillary sinus can, upon lifting the maxillary sinus at a position of placement of an implant, form and enlarge the vertical hole with ease in the remaining bone of the maxillary sinus though vertical approaching, and upon forming the lateral window below the malar bone through lateral approaching can prevent the maxillary membrane from becoming damaged, thereby ensuring continuous, safe lifting so that the operating time is shortened and the operation efficiency is maximized.

DESCRIPTION OF THE ELEMENTS OF THE DRAWINGS

| | |
|---|---|
| 100: Piezo Main Unit | |
| 10: Piezotome Operation Unit for Vertical Approaching Operation | |
| 11: Piezo Body | 12: Piezo Pole |
| 13: Piezo Tip | 14: Cutting Blade |
| 15, 25: Water Supply Hole | 16, 26: Stopper |
| 20: Piezotome Operation Unit for the Lateral Approaching Operation | |
| 21: Window Body | 22: Window Pole |
| 23: Window Tip | 24: Cutting Projection |
| 24S: Inclined Cutting Face | 30: Hand Piece |
| 40: Maxillary Sinus | 41: Remaining Bone |
| 42: Maxillary Membrane | 43: Vertical Hole |
| 44: Opening | 45: Window |

MODE FOR INVENTION

Description will now be made of exemplary embodiments of the present invention with reference to the accompanying drawings.

Figure 1:
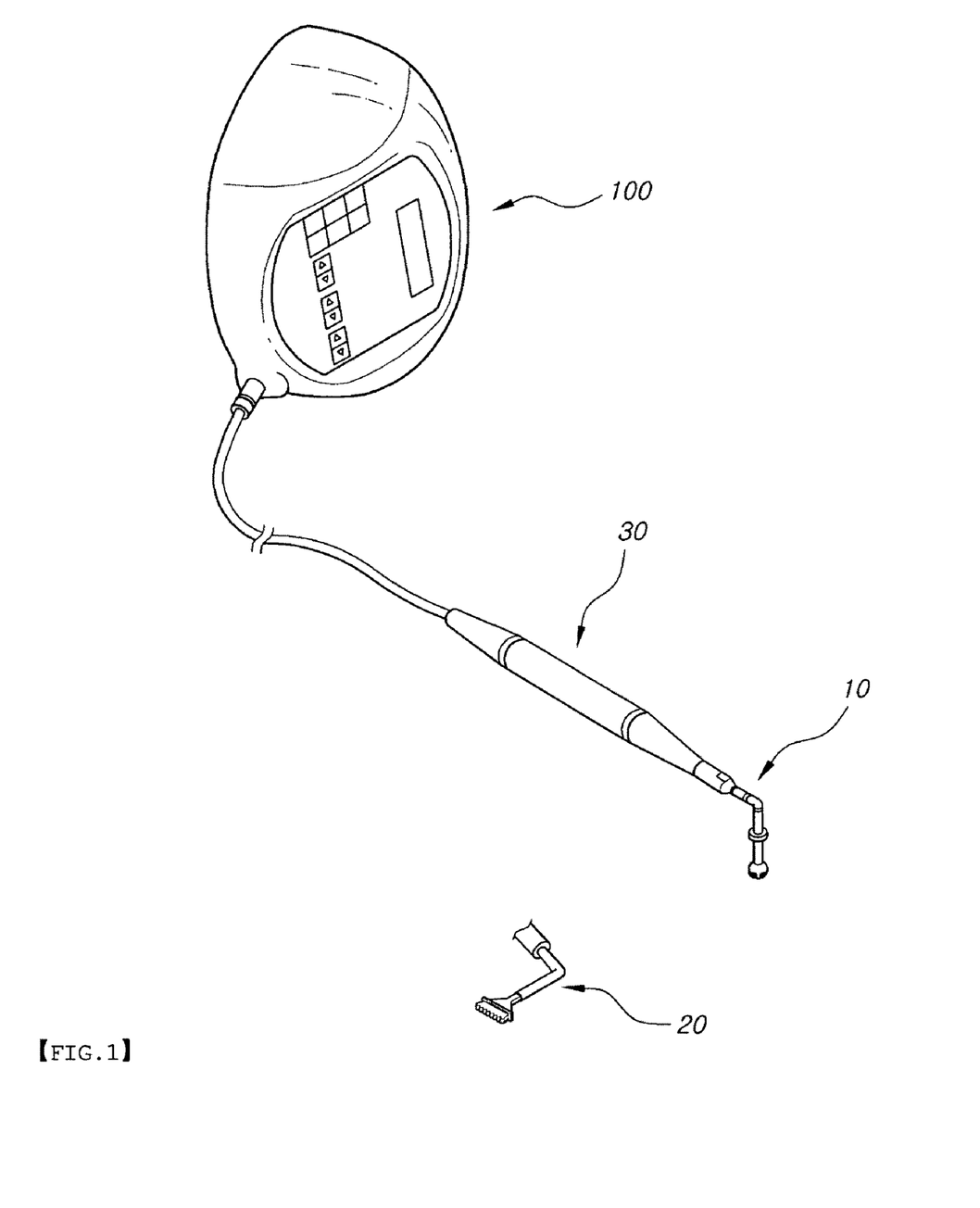
FIG. 1 is a perspective view illustrating a piezotome operation unit of the present invention in the state in which it is used, connected to a piezo main unit.
Figure 2:
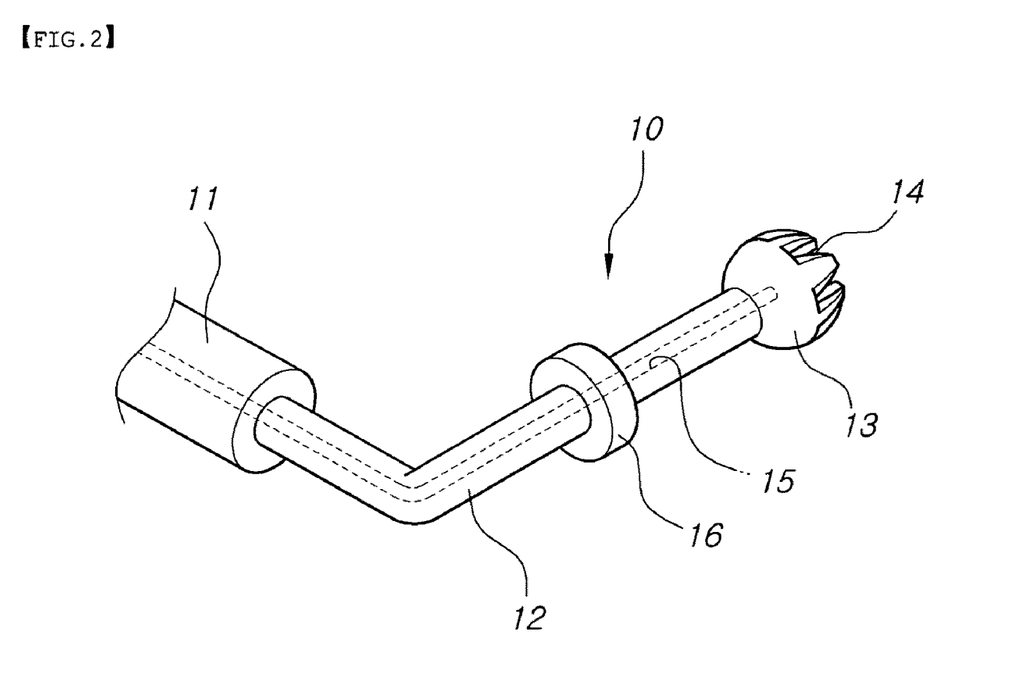
FIG. 2 is a perspective view illustrating a piezotome operation unit for a vertical approaching operation according to an embodiment of the present invention.
Figure 3:
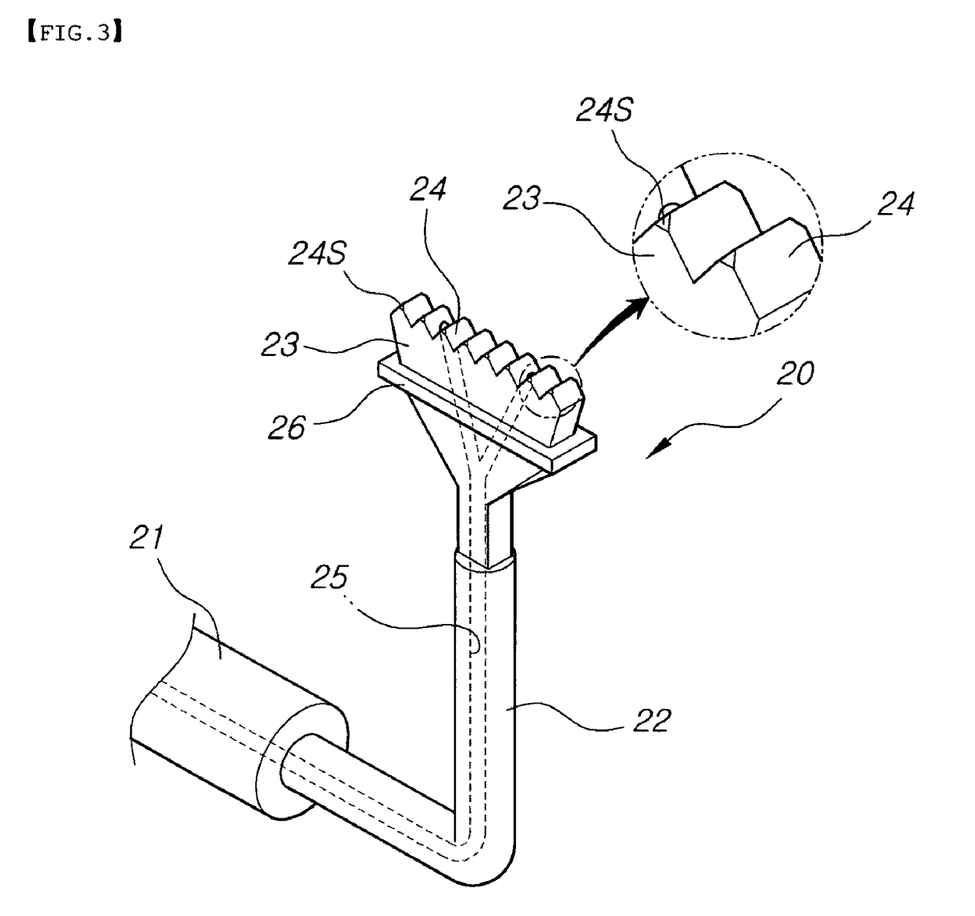
FIG. 3 is a perspective view illustrating a piezotome operation unit for a lateral approaching operation according to an embodiment of the present invention.
Figure 4:
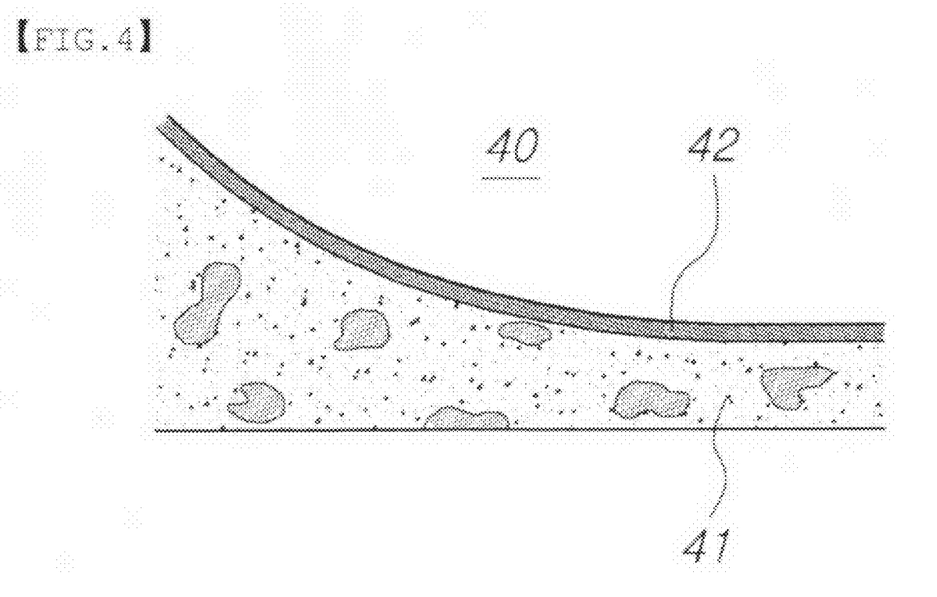
FIGS. 4 to 6 are cross-sectional views illustrating an exemplary procedure of using the piezo operation unit for the vertical approaching operation in order to form a vertical hole in the remaining bone of a maxillary sinus according to the present invention.
Figure 5:
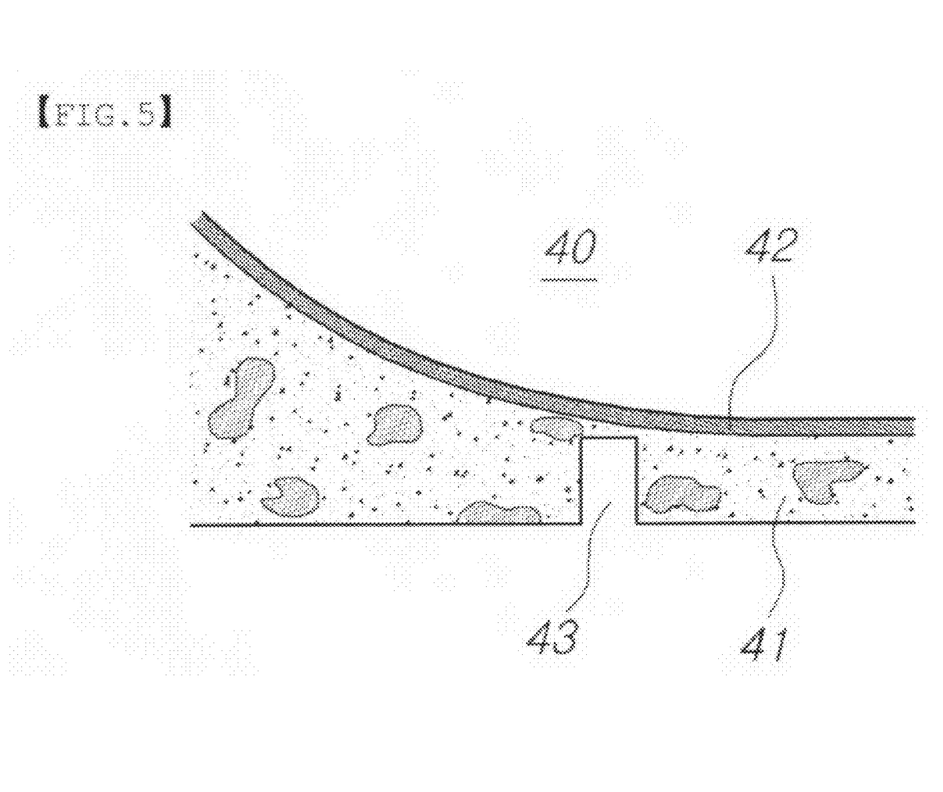
Figure 6:
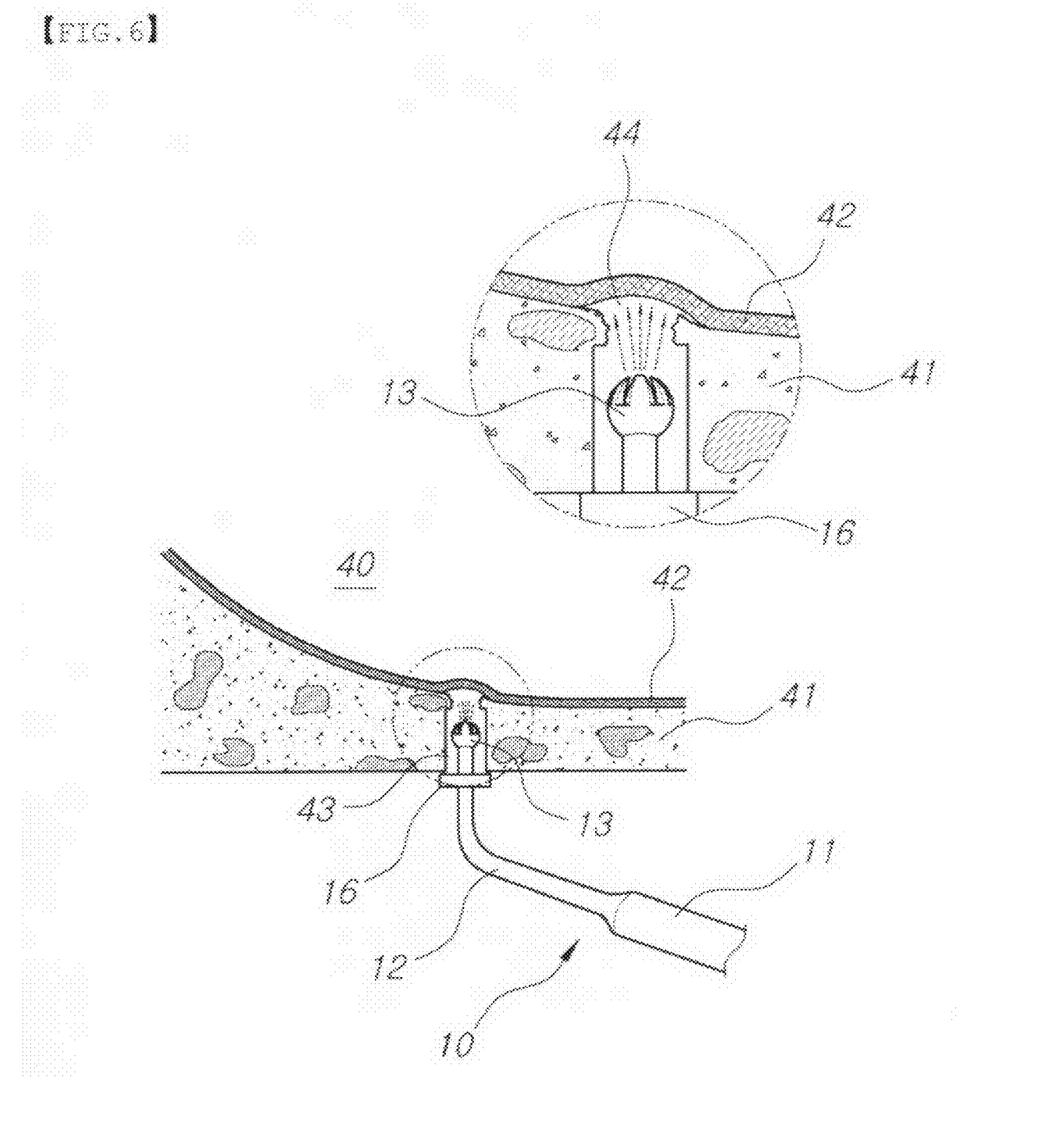
Figure 7:
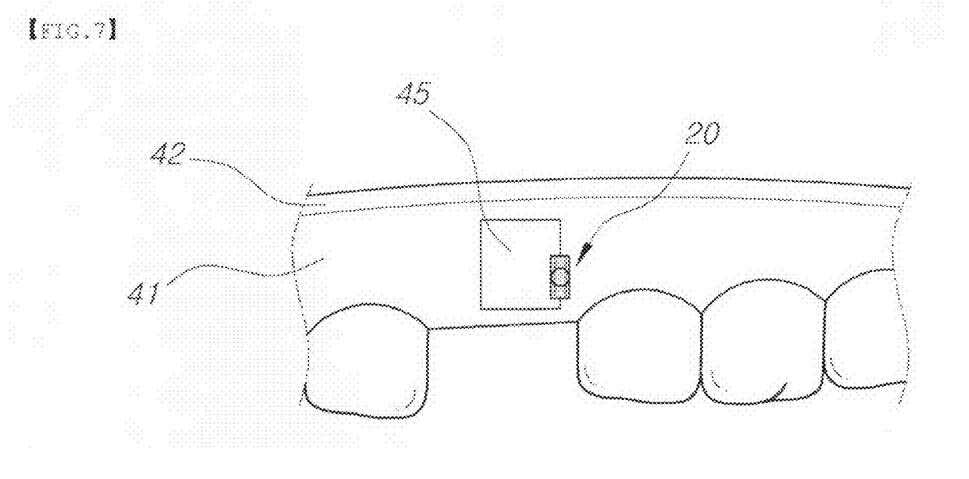
FIG. 7 is a schematic front view illustrating an example of using the piezotome operation unit for the lateral approaching operation according to the present invention.

FIG. 1 is a perspective view illustrating the state of a piezotome operation unit of the present invention in which it is used, connected to a piezo main unit, FIG. 2 is a perspective view illustrating a piezotome operation unit for a vertical approaching operation according to an embodiment of the present invention, FIG. 3 is a perspective view illustrating a piezotome operation unit for a lateral approaching operation according to an embodiment of the present invention, FIGS. 4 to 6 are cross-sectional views illustrating an exemplary procedure of using the piezo operation unit for a vertical approaching operation in order to form a vertical hole in a remaining bone of a maxillary sinus according to the present invention, and FIG. 7 is a schematic front view illustrating an example of using the piezotome operation unit for a lateral approaching operation according to the present invention.

The piezotome operation unit 10 and 20 for lifting a maxillary sinus according to the present invention is installed onto a hand piece 30 of a piezo main unit 100 so as to receive electric vibrations generated from the piezo main unit 100 and mechanically vibrate. The piezotome unit for a vertical approaching operation is used to form a vertical hole in a remaining bone of the maxillary sinus, or enlarge the vertical hole, and the piezotome operation unit 20 for a lateral approaching operation is used to form a lateral window below a malar bone or to cut a bone inside the window.

Further, the piezotome operation unit 10 for a vertical approaching operation includes a piezo body 11, an end of which is fixedly inserted into the hand piece 30, a piezo pole 12 extending from another end of the piezo body 11, and a piezo tip 13 provided on an end of the piezo pole 12. The piezo pole 12 is bent like a "┓" such that it can approach the maxillary sinus with ease. The piezo tip 13 is provided with, on its end, a plurality of cutting blades 14 at equal intervals. The overall shape of the cutting blades 14 is shaped like a hemisphere in which the respective ends thereof converge towards a leading end side of the hemisphere.

The vertical approaching type piezotome operation unit 10 includes, at the center of the inside thereof, a water supply hole 15 passing through the piezo body 11, the piezo pole 12, and the piezo tip 13. The piezo pole 12 is provided, on its outer face, with a protruding stopper 16 in order to restrict a distance of insertion according to a thickness of the remaining bone. Here, a distance between an end of the cutting blade 14 and the stopper 16 ranges from 3 mm to 8 mm with a gap of 1 mm interposed so as to allow the piezotome operation unit 10 to be easily and conveniently used according to a patient's state.

Further, the lateral approaching type piezotome operation unit 20 includes a window body 21, an end of which is fixedly inserted into the hand piece 30, a window pole 22 extending from an end of the window body 21, and a window tip 23 provided on an end of the window pole 22. The window pole 22 is bent like a "┓" such that it easily approaches the maxillary sinus.

Further, the window tip 23 is shaped like an inverted triangle, which is gradually enlarged from a lower portion to an upper portion, in order to enlarge a contact area when forming a lateral window (hole) 45 below a malar bone, and is provided, on its end, with a plurality of cutting projections 24, which are arranged linearly. Each cutting projection 24 is shaped like a triangle in which opposite upper portions thereof are formed with inclined cutting faces 24S meeting at an apex.

The lateral approaching type piezotome operation unit 20 includes, at the center of the inside thereof, a Y-water supply hole 25 which passes through the window body 21, the window pole 22, and the window tip 23, and branches out in two directions at its end. The window pole 22 is provided, on its outer face, with a protruding stopper 26, which upon forming a lateral window below a malar bone prevents the transmission of excessive load to the maxillary membrane. Here, a distance between an end of the cutting projection 24 and the stopper 26 ranges from 4 mm to 6 mm with a gap of 1 mm interposed, in order to easily and conveniently adapt the piezotome operation unit 20 to a patient depending on the patient's state.

Meanwhile, FIG. 4 illustrates the state in which a molar tooth below the maxillary sinus 40 falls out, leaving a maxillary alveolar bone as the remaining bone 41. However, in such a state, an implant cannot be directly placed into the remaining bone 41, so that bone grafting is first performed onto the corresponding section in order to thicken it.

First, as illustrated in FIG. 5, the vertical hole 43 is formed in the remaining bone 41 in such a manner that, if the remaining bone 41 is of a comparatively large thickness, the vertical hole 43 is drilled using a surgical drill with a length of the bone ranging approximately from 1 mm to 2 mm remaining from the bottom of the remaining bone, and if the remaining bone 41 is of a thin thickness of 4 to 5 mm or less, as illustrated in FIG. 6, the vertical hole 43 is formed using the vertical approaching type piezotome operation unit 10 from the beginning so as to form an opening 44 below the maxillary membrane 42.

Herein, when the remaining bone 41 is cut using the vertical approaching type piezotome operation unit 10 as shown in FIG. 2, in order to form the vertical hole 43, the maxillary membrane is lifted by the pressurization of water supplied via the water supply hole 15 provided at the center of the inside of the piezotome operation unit 10, and at the same time, the cutting is performed by vibrations of plural cutting blades 14 of the piezo tip 13, ends of which converge towards a leading end side and form a hemisphere. At this time, the stopper 16 protruding from the outer face of the piezo pole 12 effectively prevents the piezo tip 13 from, upon insertion into the maxillary sinus, excessively pushing the maxillary membrane and thus tearing the same, thereby ensuring continuous, safe operation.

Further, when the lateral window 45 is formed below the malar bone using the piezotome operation unit 20 for a lateral approaching operation as shown in FIG. 3, as illustrated in FIG. 7, the lateral window is smoothly formed without exerting an excessive stimulus to the maxillary membrane, through the process in which water is smoothly sprayed via the both branches of the Y-type water supply hole 25, which is provided at the center of the inside of the piezotome operation unit 20 so as to pass through the window body 21, the window pole 22, and the window tip 23 while its end branches out in two ways, and at the same time, the target section is brought into contact with the triangular cutting projections 24 having the inclined faces 24S of the window tip 23, which is of an inverted triangle gradually enlarged from a lower portion to the upper portion, and is smoothly applied with load from the cutting projections and is advanced slowly via vibrations, with the stopper 26, which protrudes from the outer face of the window pole 22, preventing the rapid insertion of the cutting projections into the target section.

Here, as compared to the related art in which the target section was frequently damaged by opposite sides of the cutting projections, the present invention effectively prevents such a phenomenon by the provision of the triangular cutting projections 24 configured so as to have the inclined cutting faces 24S on opposite upper sides thereof.

In another embodiment, of course, the stopper 16 which protrudes from the outer face of the piezo pole 12 of the piezotome operation unit 10 for a vertical approaching operation, or the stopper 26 which protrudes from the outer face of the window pole 22 of the piezotome operation unit 20 for a lateral approaching operation may be provided as a removable type such as a separate rubber ring or a releasable screw type structure, as well as the integral type described in the above embodiments.

Although the preferred embodiments of the piezotome operation unit for lifting the maxillary sinus according to the present invention have been described for illustrative purposes, those skilled in the art will appreciate that various modifications, additions and substitutions are possible, without departing from the scope and spirit of the invention as disclosed in the accompanying claims. Thus, it should be understood that the present invention includes all of such modifications, additions and substitutions.

The invention claimed is:

1. A piezo ultrasonic surgery unit for lifting a maxillary sinus of a patient via vertical approaching, comprising:
    a piezo main unit;
    a hand piece connected to said piezo main unit;
    a piezo body having a first end and a second end, wherein said first end is configured and dimensioned to be fixedly inserted into said hand piece of said piezo main unit;
    a piezo pole having an outer face, a first end and a second end, said first end being connected to and extending from said second end of said piezo body;
    a piezo tip provided on said second end of said piezo pole, said piezo tip having a plurality of cutting blades arranged at regular intervals thereon which define spaces therebetween, wherein said plurality of cutting blades each have a curved outer surface, and wherein said cutting blades collectively form the general shape of a hemisphere in which respective ends of said cutting blades converge towards a hemispherical pole and define a leading end of said piezo tip;
    a stopper protruding from said outer face of said piezo pole positioned to restrict the depth of insertion of said piezo tip into a patient, depending on a predetermined thickness of remaining bone; and
    wherein each of said piezo body, piezo pole, and piezo tip have a water supply channel passing through the center of each which are in fluid communication and allow water jetted therethrough to exit from said channel and, ultimately, from said piezo tip to ensure continuous, safe lifting of the maxillary sinus of the patient to prevent damage thereto during surgery.

2. The piezo ultrasonic surgery unit according to claim 1, wherein:
    said piezo pole extends from said piezo body in a linear fashion.

3. The piezo ultrasonic surgery unit according to claim 1, wherein:
    said piezo pole extends from said piezo body in a bent fashion.

4. The piezo ultrasonic surgery unit according to claim 1, wherein:
    said stopper is integral with said piezo pole.

5. A piezo ultrasonic surgery unit for lifting a maxillary sinus of a patient via lateral approach, comprising:
    a piezo main unit;
    a hand piece connected to said main unit;
    a body having a first end and a second end, wherein said first end is configured and dimensioned to be fixedly inserted into said hand piece of said piezo main unit;
    a pole having an outer face, a first end and a second end, said first end being connected to and extending from said second end of said body such that said pole easily approaches the maxillary sinus;
    a tip provided on said second end of said pole, having a plurality of cutting projections thereon for insertion of a graft material, wherein said tip has a base portion and an upper portion, said base portion is shaped like an inverted triangle which is gradually enlarged from a lower portion towards said upper portion, and wherein said cutting projections are provided on said upper portion of said tip and are arranged linearly in a row at regular intervals to form a sawtooth-like pattern, and wherein each cutting projection is generally shaped like a triangular prism having an upper vertice which defines an apex having two opposite ends which are beveled to form two downwardly angled triangular-shaped inclined cutting faces at said opposite ends of said apex;
    a stopper protruding from said outer face of said pole positioned to, upon forming a lateral window below a malar bone, restrict the depth of insertion of said tip into a patient, depending on a predetermined thickness of remaining bone and, in turn, prevent an excessive load from being transmitted to the maxillary sinus; and
    wherein each of said piezo body, piezo pole and piezo tip have a water supply channel passing through the center of each, which are in fluid communication and wherein said water supply channel is Y-shaped and has two outer ends which branch out in two directions and which allow water jetted therethrough to exit from said channel and, ultimately, from said tip to ensure continuous, safe lifting of the maxillary sinus of the patient to prevent damage thereto during surgery.

6. The piezo ultrasonic surgery unit according to claim 5, wherein:
    said pole extends from said body in a linear fashion.

7. The piezo ultrasonic surgery unit according to claim 5, wherein:

said pole extends from said body in a bent fashion.

8. The piezo ultrasonic surgery unit according to claim 5, wherein:
said stopper is integral with said body.

* * * * *